(12) United States Patent
Hill et al.

(10) Patent No.: US 9,345,852 B2
(45) Date of Patent: May 24, 2016

(54) FLOAT TENT

(71) Applicant: Zen Float Co. LLC, Murray, UT (US)

(72) Inventors: William Charles Hill, Macclesfield (GB); Shane Jospeh Stott, Salt Lake City, UT (US); Sean Gale Stott, Cottonwood Heights, UT (US)

(73) Assignee: ZEN FLOAT CO. LLC., Murray, UT (US)

( * ) Notice: Subject to any disclaimer, the term of this patent is extended or adjusted under 35 U.S.C. 154(b) by 199 days.

(21) Appl. No.: 14/035,494

(22) Filed: Sep. 24, 2013

(65) Prior Publication Data

US 2015/0087893 A1 Mar. 26, 2015

(51) Int. Cl.
*A61M 21/00* (2006.01)
*E04H 15/02* (2006.01)
(Continued)

(52) U.S. Cl.
CPC ........... *A61M 21/0094* (2013.01); *A61M 21/02* (2013.01); *E04H 4/0056* (2013.01); *E04H 15/02* (2013.01); *E04H 15/12* (2013.01); *A61H 2033/0008* (2013.01); *A61H 2033/0083* (2013.01); *A61H 2033/048* (2013.01); *A61H 2201/0157* (2013.01); *A61H 2201/0161* (2013.01); *A61H 2201/10* (2013.01); *A61M 2021/0027* (2013.01); *A61M 2021/0044* (2013.01); *A61M 2021/0066* (2013.01); *A61M 2205/3368* (2013.01); *A61M 2205/3569* (2013.01); *A61M 2205/3592* (2013.01); *A61M 2205/3653* (2013.01); *A61M 2205/42* (2013.01); *E04H 15/324* (2013.01)

(58) Field of Classification Search
CPC ............ A61M 21/0094; A61M 21/02; A61M 2021/0044; A61M 2021/0027; A61M 2021/0066; A61M 2205/42; A61M 2205/3653; A61M 2205/3592; A61M 2205/3569; A61M 2205/3368; E04H 15/12; E04H 15/02; E04H 15/324; E04H 15/20; E04H 9/00; E04H 2015/203; E04H 2015/208; E04H 2015/205; E04H 2015/206; E04H 2015/207; A61H 2201/0157; A61H 2201/0103
See application file for complete search history.

(56) References Cited

U.S. PATENT DOCUMENTS 3,683,427 A * 8/1972 Burkholz ................ E04H 4/108
135/119
4,000,749 A * 1/1977 Busco ............................ 600/21
(Continued)

OTHER PUBLICATIONS

DU20 Holistic Oasis "The Floating Experience" accessed online at http://www.du20.com/the_floating_experience on Jun. 23, 2015, available online on Mar. 14, 2013.*
(Continued)

*Primary Examiner* — Navin Natnithithadha
*Assistant Examiner* — Kaylee Wilson
(74) *Attorney, Agent, or Firm* — Alpine IP PLLC

(57) ABSTRACT

A float tent can include: a frame having a pool frame portion with a tent frame portion thereof over the pool frame portion; a tent having the tent frame portion, the tent having a closable opening; and a pool having the pool frame portion, the pool having pool sides dimensioned to hold at least 8 inches of water and having a pool base dimension sufficient for a person to lay in the pool without touching pool sides. The tent can include tent walls having an angle that inhibits condensation drip, the angle being with respect to the pool base, such as at least 4.5 degrees. The tent can include a material that is opaque. The float tent can include a heater configured to heat the water to skin temperature of the person. The float tent can include a water circulation pump and filter.

15 Claims, 7 Drawing Sheets

(51) Int. Cl.
  *E04H 15/12* (2006.01)
  *A61M 21/02* (2006.01)
  *E04H 4/00* (2006.01)
  *E04H 15/32* (2006.01)
  *A61H 33/00* (2006.01)
  *A61H 33/04* (2006.01)

(56) References Cited

U.S. PATENT DOCUMENTS

| | | | | |
|---|---|---|---|---|
| 4,332,112 A | * | 6/1982 | Hsu | E04H 15/20 52/2.21 |
| 4,470,404 A | * | 9/1984 | Kremen | F24J 2/0461 126/564 |
| 5,617,681 A | * | 4/1997 | Lyons | E04H 3/16 135/124 |
| 6,487,734 B1 | * | 12/2002 | First | E04H 4/108 4/498 |
| 2010/0031434 A1 | * | 2/2010 | Tassone, Jr. | E04H 4/0043 4/506 |
| 2011/0247970 A1 | * | 10/2011 | Evingham | B01D 29/21 210/85 |

OTHER PUBLICATIONS

FloatSeattle "Manage Pain" accessed oline at http://floatseattle.com/manage-pain/ on Jun. 23, 2015, avaliable online on Jan. 21, 2013.*
Culllen ("Sea Water Pool", www.clean-pool-and-spa.com/sea-water-pool.html; accessed online on Oct. 21, 2015, available online on Jan. 6, 2011).*
Bucknell University "Swimming Information" www.bucknell.edu/athletics/recreation-services/swimming-information.html, Accessed Online on Feb. 10, 2016.*

* cited by examiner

FLOAT TENT

BACKGROUND

Floatation therapy is a medical treatment using sensory deprivation within a floatation tank or float room. Years of well-documented tests show that floatation tank therapy not only has an immediate effect on pain relief and elimination of stress, it also promotes 'whole-brain' thinking. Many athletes, writers, and artists have experienced enormous benefits from floatation therapy utilizing floatation tanks.

There remains a need in the art for improved float tank or float tank-like systems.

SUMMARY

In one embodiment, a float tent can include: a frame having a pool frame portion with a tent frame portion thereof over the pool frame portion; a tent having the tent frame portion, the tent having a closable opening; and a pool having the pool frame portion, the pool having pool sides dimensioned to hold at least 8 inches of water and having a pool base dimension sufficient for a person to lay in the pool without touching pool sides. In one aspect, the tent can include tent walls having an angle that inhibits condensation drip, the angle being with respect to the pool base. In one aspect, the angle is at least 4.5 degrees. In one aspect, the tent includes a material that is opaque. In one aspect, the float tent includes a heater configured to heat the water to skin temperature of the person. In one aspect, the float tent includes a water circulation pump and filter. In one aspect, the float tent includes all tent walls having the condensation drip inhibiting angle. In one aspect, the tent includes a tent member and the pool includes a pool member that is separate from the tent member. In one embodiment, the frame includes frame supports and frame coupling members that are configured for assembling and disassembling the float tent. In one aspect, each tent wall is a triangle with a base dimensioned with a pool wall of the pool.

In one embodiment, a method of floatation can include: providing the float tent as described herein, the float tent having water in the pool that has at least about 3.5% salinity and at least about 95° F.; and floating a subject in the water of the pool without touching the pool base or pool walls. In one aspect, the method can include inhibiting light and/or sound from entering into the float tent. In one aspect, the method can include the subject floating without their arms or legs touching another part of their body. In one aspect, the method can include the user floating until having one or more of the following: diminished pain; accelerated healing; spinal decompression; stress relief; mental relaxation; enhanced creativity and learning; pregnancy relief; relief from depression and/or anxiety; strengthened immune system; attainment of a more restful sleep; increased energy; enhanced mental focus; improved anger management; deep meditation; or combinations thereof. In one aspect, the method can include the user floating until improving: arthritis, back pain, premenstrual tension, postpartum depression, asthma, migraine headaches, multiple sclerosis, cardiovascular conditions, osteoporosis, synovitis, fibromyalgia, or combinations thereof.

In one embodiment, a float tent kit can include un-assembled components of the float tent as described herein. Such a float tent kit can include: a float tent frame; a pool base configured to retain water, the pool base having pool sides dimensioned to hold at least 8 inches of water and having a pool base dimension sufficient for a person to lay in the pool without touching pool sides; and a tent having a closable opening. The float tent frame, pool base, and tent are configured to be assembled into a float tent. The float tent frame has a pool frame portion with a tent frame portion thereof over the pool frame portion. The tent is configured to be received onto the tent frame portion. The pool base is configured to be received onto the pool frame portion. In one aspect, the float tent kit can include a heating unit. In one aspect, the float tent kit can include a water circulation pump and filter. In one aspect, the float tent kit can include one or more of: a salt reservoir, a UV unit; an ozone unit; a timer; a light device; or a sound device. In one aspect, the float tent kit can include an amount of salt sufficient to create water salinity in the pool base of at least 3.5% salinity.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
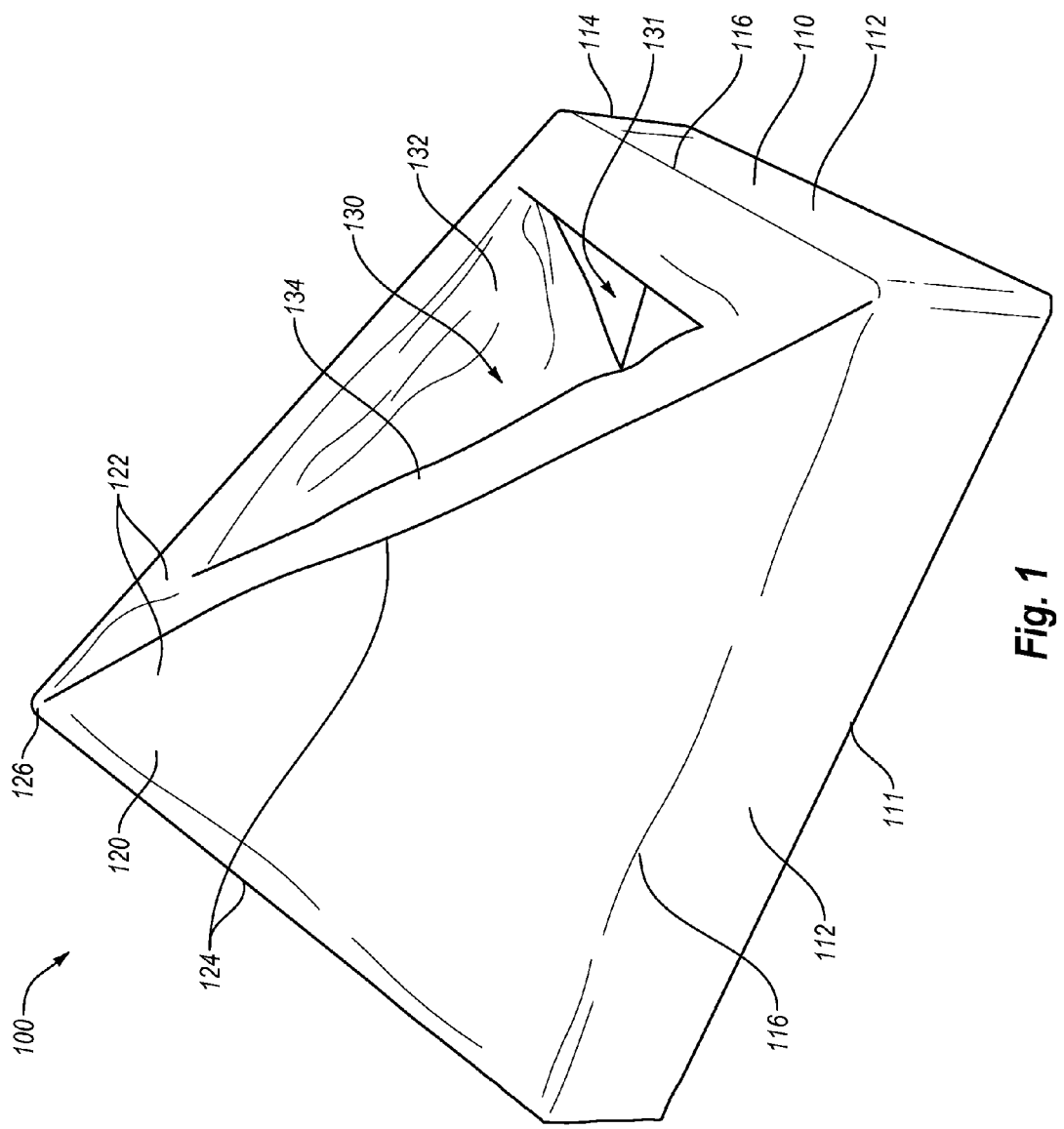
FIG. 1 includes a perspective view of an embodiment of a float tent.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention includes a float tent that can be used in relaxation therapies, such as floatation therapy and sensory deprivation therapy, among others. The float tent can include a pool base with a tent over the pool base. The pool base can have a sufficient pool height so that a subject can float in the pool base without touching the bottom. The pool can be dimensioned with a width and/or length for the subject to be able to float without touching a side of the pool. The tent can have a height to allow for the subject to enter and exit the float tent. The tent height can be modified and adjustable. The float tent can configured to be collapsible and portable, which can be accomplished with the tent and/or pool base to be flexible, such as by being canvas or other thin watertight material, and the tent and/or pool base supporting frame structure being collapsible (e.g., telescoping support poles and/or articulating joints connecting the support poles).

The float tent can be configured as a lightproof, waterproof tent designed for a person to lie down in and float within without touching the walls of the pool base. The pool base can be dimensioned to be at least about 10 inches to at least about 24 inches in height to allow the person to float. In one example, the pool base can be dimensioned to contain salt water at a depth of about 8 inches to about 12 inches. The float tent can have a canvas pool base that is waterproof-watertight so as to retain the water therein without leakage. In order to be waterproof-watertight, the pool base may be only canvas or treated canvas or polymer-lined canvas, or other so as to be capable of functioning as a pool to retain water.

The tent can be integrated with the pool base or couplable thereto so as to be capable of being removed from the pool base. The tent top can be configured as any type of tent that extends upward from the pool base. The pool base forms the bottom of the tent. The tent can be configured as a common tent with an opening that can be closed and it may include air vents or the like. The material of the tent can be opaque so that no light penetrates into the internal area of the tent.

The person can enter the float tent via a tent opening in the tent, and then lie down in the salt water, which can have an appropriate salt content so that the person floats without aid or swimming action. That is, the person can lie in the salt water and float without movement. In an example, the water can include a mixture of about 800 pounds of Epsom salt. The water can be heated to body temperature, such as with a water heater. This salt water can suspend the person at the top of the water creating a near zero gravity environment by effortlessly floating and maintaining the resting body at the top of the water. The person can have a complete lack of sensations while floating, which lack of sensations can include the environment in the float tent to be devoid of: gravity sensations, light, sound, and feeling of temperature difference from body, as well as other sensations. The experience in the float tent can be sufficient to remove sensations so that the mind can relax to a state of meditation or clearness. The person can spend various amounts of time within the float tent, which can be measured or set with a timer device, such that the time can vary from 30 minutes to a few hours. The time of floating in the float tent can be sufficient to allow the person to feel disconnected from the outside world, and to aid such a disconnectedness and relaxation state. All electronic devices or outside environmental distractors can be removed or turned off. In one aspect, the float tent can be used in a room that is isolated without electronic components that can be distracting. For example, the person's mobile phone can be left outside of the room to enhance the disconnectedness and relaxation state.

FIG. 1 illustrates an embodiment of a float tent 100 having a pool 110 and a tent 120 with an opening 130 that allows a subject to enter into the float tent 100 for floatation and/or relaxation and/or sensory deprivation or for any other reason. The pool 110 can include a pool base 111, which is the bottom of the pool 110. The pool 110 includes at least one pool wall 112 that defines the side of the pool 110, where a single pool wall 112 can be used for a circular float tent 100 and four pool walls 112 can be used for a square or rectangular float tent 100. The pool wall(s) 112 can extend upward from the pool base 111. The pool base 111 and pool walls 112 can be a single material or sheet or member stitched or otherwise manufactured into the shape of a pool, or the pool base 111 and one or more of the pool walls 112 can be different materials or sheets or members that are coupled together to form the pool 110, where such manufacture forms the pool 110 capable of holding water without leakage. Waterproofing can be used at any seam or junction of materials in the pool 110. Any number of pool walls 112 can be used, depending on the shape of the pool 110. The pool 110 includes pool corners 114 when more than one pool wall 112 is used, where the pool corners 114 are the intersection between adjacent pool walls 112. The pool walls 112 are generally vertical, but may vary up to about 45 degrees or more or as desired. Structural supports can be used to define the shape and stability of the pool walls 112, and thereby of the pool 110 and float tent 100 in general.

The tent 120 is coupled to the pool 110. As shown, the vertical walls at the bottom are the pool walls 112 of the pool 110, and the sloped walls are tent walls 122. The tent walls 122 are separated from the pool walls 112 by a pool edge 116, which is also a tent edge; however, the pool edge 116 defines the top level of water in the pool 110. The tent walls 122 are also separated from each other by tent corners 124. While the tent 120 can include any number of tent walls 122, one tent wall 122 can form a circular or domed tent 120, where four tent corners 124 can be included in a tent 120 that has a square or rectangular cross-section. The number of tent corners 124 can match the number of pool corners 114; however, numbers may vary or be different depending on design. At least one of the tent walls 122 includes a tent opening 130 that allows for access into the inside 131 of the float tent 100. The tent opening 130 can be defined by a tent flap 132 that opens and closes to open and close the tent 120. The tent flap 132 is shown to open by being unattached from a flap receiver 134 that forms an edge of the tent opening 130 when the tent flap 132 is detached from the flap receiver 134. However, any configuration of a tent opening 130 that is used in traditional tents can be used in the present invention. For example, two tent flaps 132 can be used that together form an upside-down "T" shape as is common with camping tents, which tent flaps can be fastened together to close the tent 120. An attachment mechanism (not shown) can be used to close the tent flap(s) 132, which can be snaps, Velcro (e.g., hook and eyelet), zipper, magnetic (e.g., magnets in the tent flap 132 and flap receiver 134), or any other fastening means that can close the tent 120.

The present configuration illustrated in FIG. 1 and described herein can be beneficial for reducing noise or lights from entering into the float tent 100, and it can be useful for preventing water dripping from the tent 120 into the pool 110. The material of the float tent 100 for at least the pool walls 112 (optionally for the tent walls 122) can be waterproof or water resistant or configured for water retention for use as a pool 110, where examples of the material can be waterproof canvas, plastic, polymeric, hydrophobic material, or other well-known waterproof material that can be used for a flexible pool. The angle of the tent walls 122 relative to horizontal can be configured to reduce condensation drip, which angles are described in more detail herein.

Figure 1A:
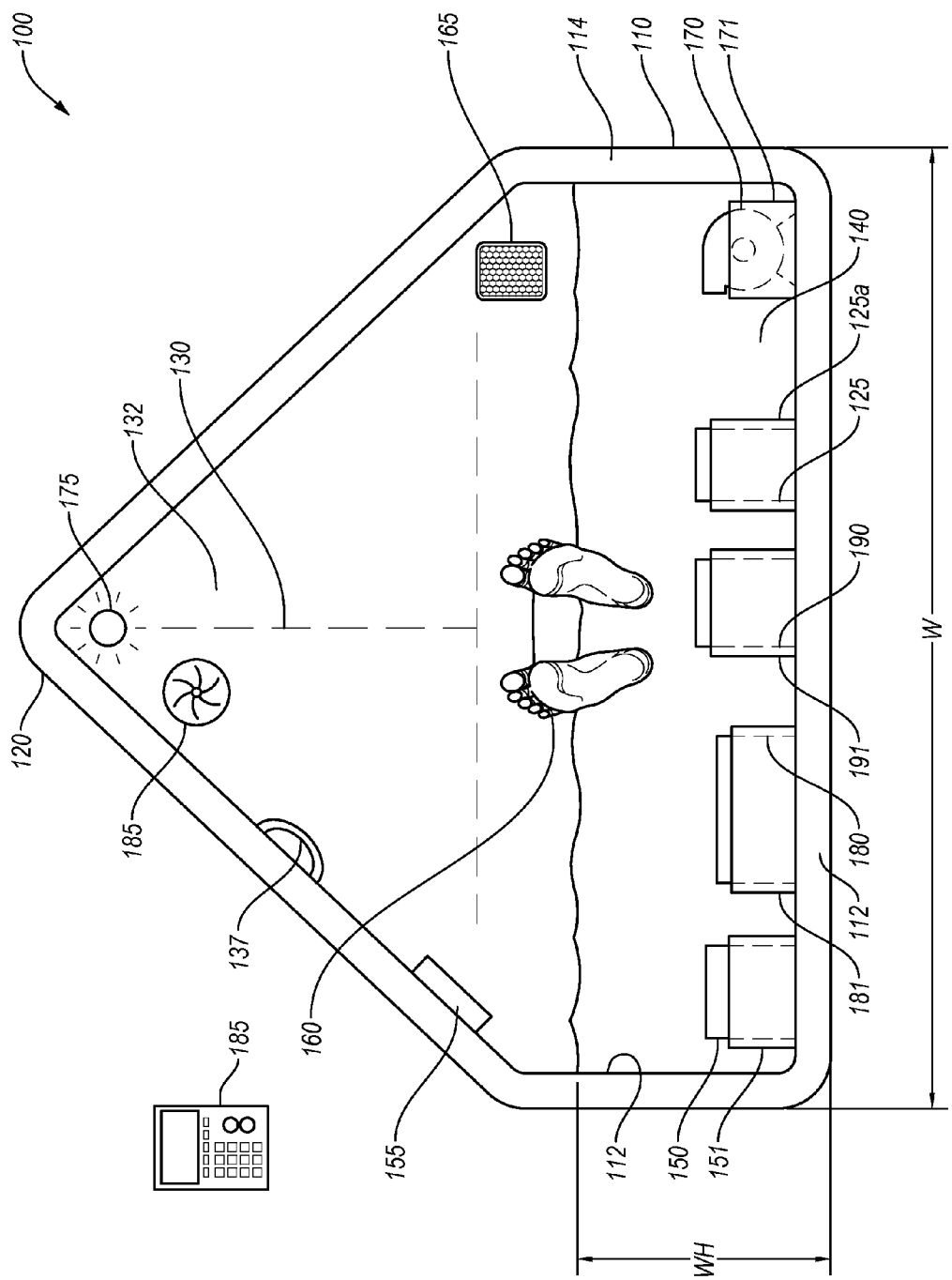
FIG. 1A includes a front cross-sectional view of the float tent of FIG. 1.

FIG. 1A illustrates a cross-sectional front view (e.g., from the end with the tent flap 132, but showing an upside-down "T" formed by the tent flaps 132) of the embodiment of the float tent 100 of FIG. 1. The float tent 100 also includes the pool 110 having water 140 with a water height WH, which can be about 6 inches, 8 inches, 10 inches, 12 inches, 14 inches, 16 inches, 18 inches, 20 inches, or more or any range between the recited values. The height PH of the pool walls 112 can be configured to accommodate such water height WH, such as the water height WH plus about 2 inches, 4 inches, 6 inches, 8 inches, 10 inches, 12 inches, 14 inches, 16 inches, 18 inches, 20 inches, or more or any range between the recited values. The pool 110 can have the pool base 111 with a width W that can vary depending on the size of the subject to use the float tent 100 on the space available for the float tent 100 or for any other reason, such as being dimensioned for the subject to float with arms and legs fully extended outward or floating with the arms and legs close to the body. Some examples of width W of the pool base 111 can be at least about 2 feet, 3 feet, 4 feet, 5 feet, 6 feet, 7 feet, 8 feet, or more or any range between the recited values. The length L of the pool base 111, as per FIG. 1B or 1C, can vary, such as at least about 6 feet, 7 feet, 8 feet, 9 feet, 10 feet, or more or any range between the recited values. The dimensions of the pool base 111 can be configured to accommodate a floating human, such as a child, teen, or adult, male or female.

In one embodiment, the dimensions of the float tent can be increased to accommodate obese and morbidly obese individuals. In this instance, the water height WH may have to be increased significantly up to 2 feet, 2.5 feet, 3 feet, 3.5 feet, 4 feet, 4.5 feet, or 5 feet or more in some exceptional circumstances. Accordingly, an embodiment of the invention includes obtaining dimensions of a subject user, and dimensioning the float tent to accommodate the size of the user subject so that the user subject can float in the pool without touching the pool base.

The pool 110 can include components that allow for the functionality of a subject 160 floating and use as a float pool. Such components can include a heater 150, circulation pump 170, UV/ozone device 180, filter 190, salt reservoir 125, or other component that can be at least partially submerged in water 140. While FIG. 1A shows the components on the pool base 111, such components may be on the pool wall 112 or configured to float or partially float in the water 140. Also, the pool 110 can include compartments for each of the components, such as a heater compartment 151, circulation pump compartment 171, UV/ozone device compartment 181, filter compartment 191, salt reservoir compartment 125a, or other component compartment that can be at least partially submerged in water 140. The compartments may be formed into the pool base 111 and/or pool wall 112, or coupled thereto, or separate therefrom, or removably attachable thereto (e.g., via Velcro). The compartments may be of a different material from the material of the pool base 111 and/or pool wall 112, or may be the same material, or a portion of the pool base 111 and/or pool wall 112 may form the compartments. The compartments may be rigid or flexible similarly to the flexibility of the pool base 111 and pool walls 112. The location of the components in the pool can vary, and may be distributed about the perimeter, such as at a front where the head of the subject 160 may be located or on the sides or at the back where the feet are located during floating.

The tent 120 may also include components that can allow for the functionality of relaxation, meditation, sensory deprivation, or the like; not all of these components need to be used in all instances. The tent 120 can include components such as a timer 155 (e.g., to time the floatation duration), sound device 165 (e.g., any device that plays sound ranging from music to ambient sounds, such as waves, crickets, heartbeat, or other), light device 175 (e.g., to provide one or more lights of one or more colors or changing colors or to simulate stars or other), fan 185, vent 195 (e.g., to vent air, humidity, smells, or other from the inside 131 to outside the tent 120), or others.

In one aspect, a controller 187 can be used to control any of the components of the float tent 100, such as those in the pool 110 or tent 120. The controller 187 can be wired to the components, or the controller 187 and components can be configured to be wireless for wireless control of the components. In one example, the controller 187 is a handheld communication device (e.g., Droid, iPhone, tablet, etc.) with an application that functions as a controller application.

The tent 120 may also include one or more grab handles 137 to facilitate entry into the float tent 100 or to facilitate rising from the water or exiting the float tent 100.

Figure 1B:
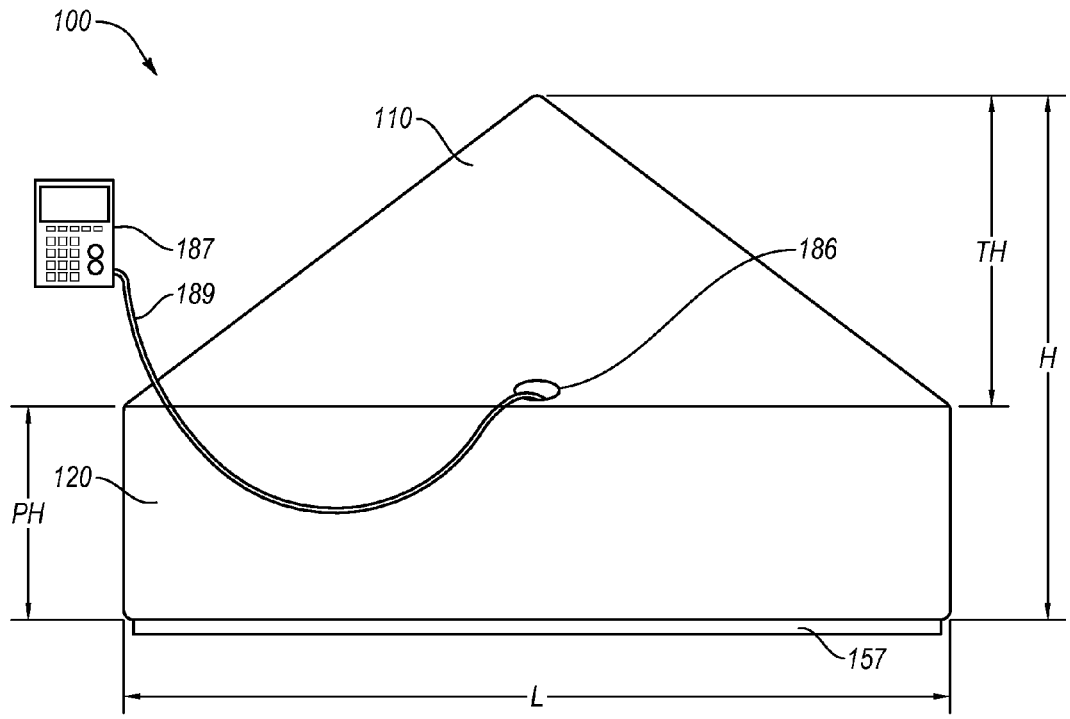
FIG. 1B includes a side view of the float tent of FIG. 1.

FIG. 1B shows a side view (e.g., view of long side) of the float tent 100 of FIGS. 1 and 1A. As shown, the tent has a tent height TH that can vary as desired or as configured for the dimensions of the pool base 111 and the slope of the tent walls 122. The slope of the tent walls 122 may or may not be configured for inhibiting condensation on the inner surface from dripping into the pool 110. Generally, the tent height TH (e.g., from pool edge 116 to tent tip 126) can vary such as from at least about 0.5 feet, 1 foot, 2 feet, 3 feet, 4 feet, 5 feet, 6 feet, 7 feet, 8 feet, 9 feet, 10 feet, or more or any value or range between the recited values. The height H of the float tent 100 can be the pool height PH plus the tent height TH. Also, the tent height TH can be calculated as described herein to provide an angle of the tent walls 122 that inhibits condensation dripping.

FIG. 1B also shows that the tent 120 has a port 186 for cords 189 to pass therethrough, where such cords 189 may be operably coupled to one or more components of the float tent 100 to the controller 187. The port 186 may also be in the pool 110 or junction between the pool 110 and tent 120. The port 186 may be sealed or sealable or self-sealable, or include a flap or other means for closing the port 186.

In one embodiment, the float tent can include a radiant heater, which is shown as radiant heater 157, as shown in FIG. 1B.

Figure 1C:
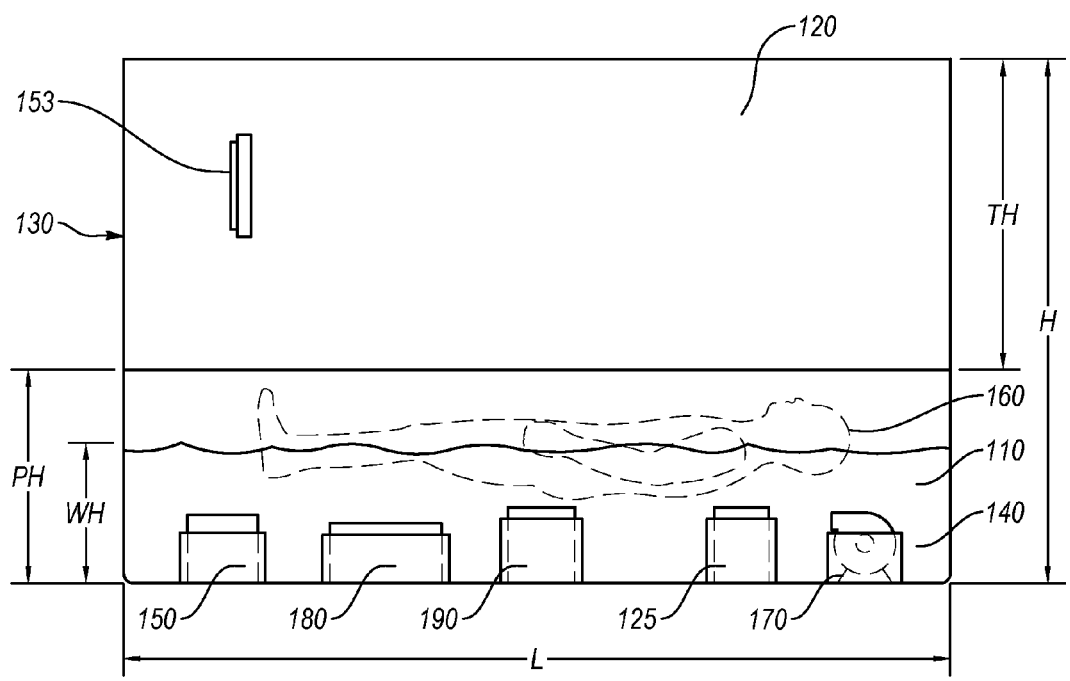
FIG. 1C includes a side view of another embodiment of a float tent.

FIG. 1C shows a side view (e.g., view of long side) of another embodiment of the float tent 100, which has a rectangular side profile with vertical ends and a sloped side. The sloped side can be sloped as described herein. The sloped side may include one or more vent slits 153.

Figure 2:
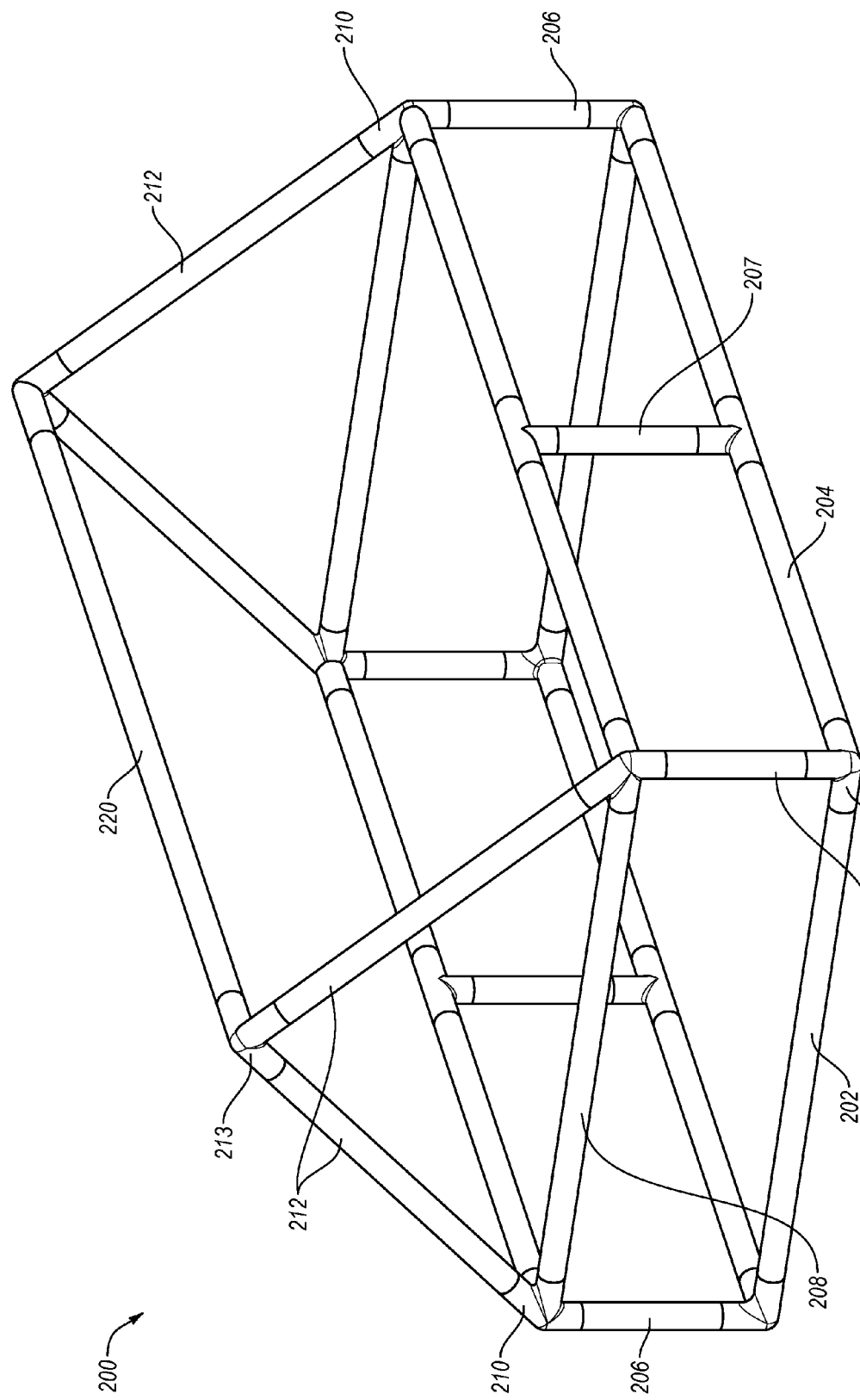
FIG. 2 includes a perspective view of a frame structure of an embodiment of a float tent.

FIG. 2 illustrates an embodiment of a float tent frame 200 for an embodiment of a float tent that is square or rectangular and has a tent with a flat top and sloped sides; however, the shape and configuration and number of frame components may vary to conform with embodiments described herein or derived therefrom. The frame 200 is shown to include a base end support 202 that is coupled with two corner supports 206 through a coupling member 214, and that is coupled to two base side supports 204 through the same coupling members 214 (or can be different coupling members). An edge end support 208 is coupled to the same two corner supports 206 through coupling members 210, and is coupled to two edge side supports 211 through the coupling members 210 (or different coupling members). The side is shown to have a side middle support 207 that is coupled to the base side support 204 through a coupling member 214 and is coupled to the edge side support 211 through a coupling member 210. The edge end support 208 and both corresponding edge side supports 211 are coupled to two sloped roof supports 212 that are, in turn, coupled together at the top by a top coupling member 213. The roof supports 212 may all be coupled together with a single coupling for a triangle side tent. However as shown, the roof supports 212 can be coupled to a top cross support 220 through the top coupling member 213. The base of the side can include a single base side support or a plurality of base side supports extending from end to end. The other end can be configured as the end shown. Also, the other side can be configured as the side shown. While not shown, the end can also include an end middle support similar to the side middle support 207, and with appropriate coupling members.

While the coupling members of FIG. 2 are shown generically, the coupling members can have individual members that receive the separate supports, and the individual members can be at the appropriate angles with respect to each other to form the shape of the float tent frame 200. The members can be tubes that are dimensioned to receive the supports therein, and may be coupled thereto or fastened thereto, such as by snap fit or button coupling (e.g., button that is pressed to receive or release and then released to protrude for the coupling), or any other coupling member that can allow for removable coupling of the coupling members and supports. For example, the bottom corner can include a coupling member that has two horizontal members and one vertical member that are orthogonal. An edge corner coupling member can include two horizontal members and one vertical member that are orthogonal along with a sloped member for the roof. A middle coupling member has two horizontal members that are aligned and one vertical member that is orthogonal with the two horizontal members.

The embodiments of the float tent have been described herein with a pool for the bottom portion and a tent for the top portion. These two portions may be coupled together or may be integrated (e.g., sewn or welded together with waterproof seams) or otherwise formed as illustrated and described. They may be made of the same materials or different materials. However, the float tent can be configured with three separate elements: the float tent frame; the pool shaped by the frame and coupled therewith; and the tent draped over the frame and optionally coupled therewith. This configuration allows for the tent to drape over the frame and over the sides of the pool.

Figure 3:
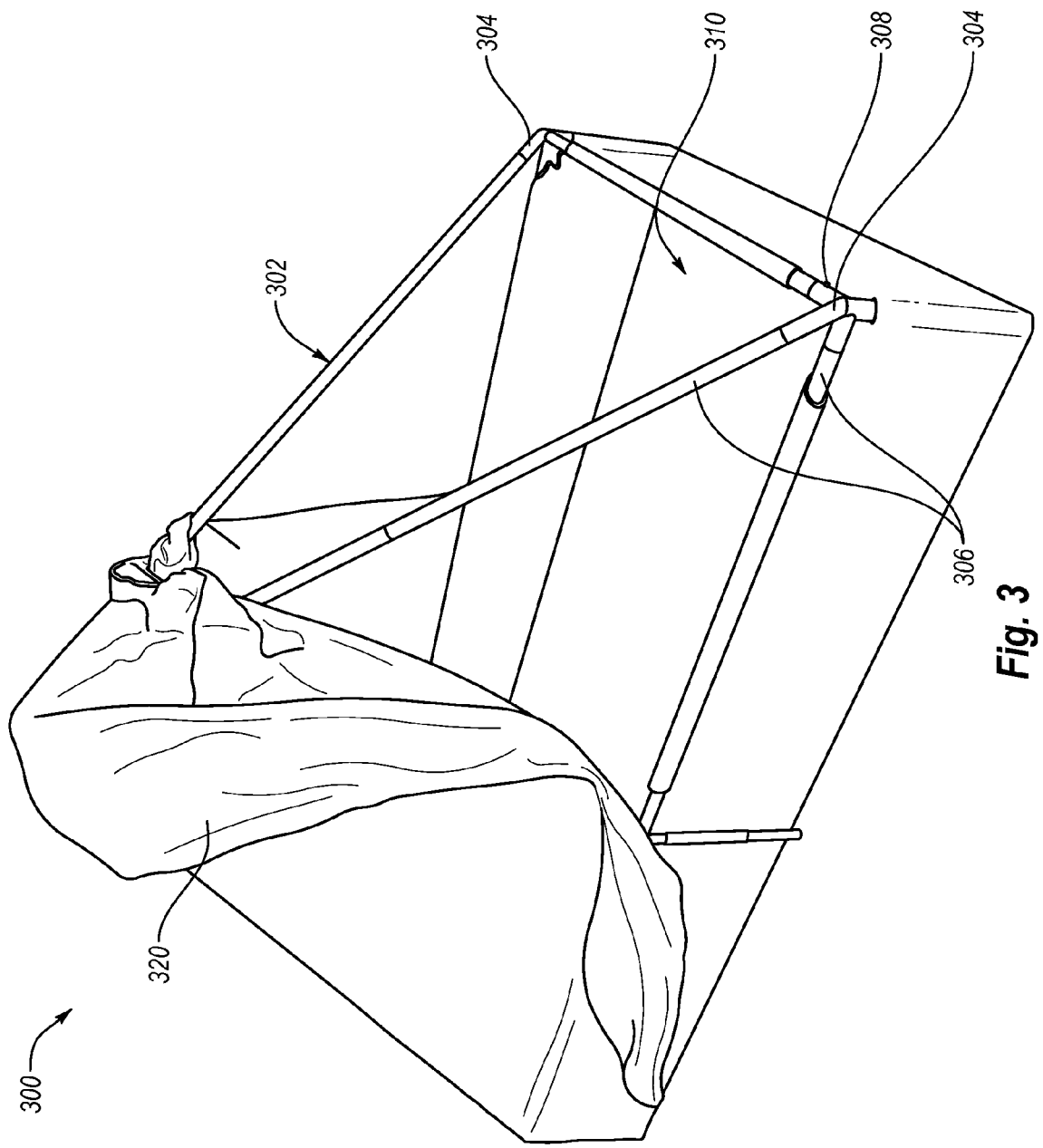
FIG. 3 includes a perspective view of the float tent of FIG. 1 with the tent draped over the frame and pool base.

FIG. 3 illustrates an embodiment of a float tent 300 that includes three separate elements: the float tent frame 302; the pool 310 shaped by the frame 302 and coupled therewith; and the tent 320 draped over the frame 302 and optionally coupled therewith. The tent 320 also drapes over the sides of the pool 310. The frame 302 includes coupling members 304 that include separate tubular members for each support member 306, with button coupling features 308.

Figure 4:
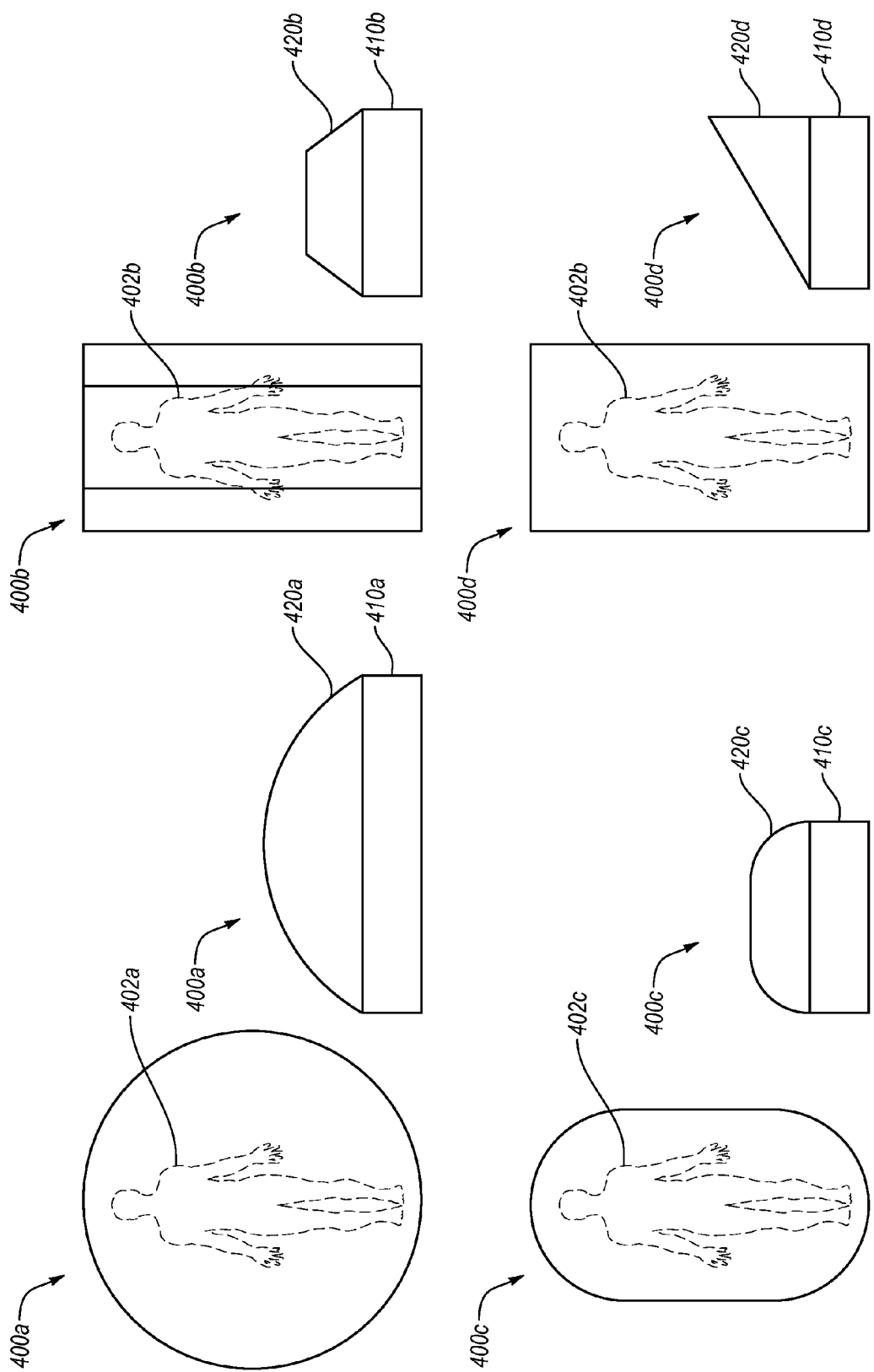
FIG. 4 includes illustrations of embodiments of shapes of float tents.

FIG. 4 illustrates different shapes of the float tent, which are not limited because other shapes may be used. The parameters should allow for a subject (e.g., 402a, 402b, 402c, 402d) to float while relaxed without touching the perimeter edges. For example: the float tent 400a can have a circular-shaped pool 410a for a subject 402a to float in with a domed tent 420a; the float tent 400b can have quadrilateral-shaped pool 410b for a subject 402b to float in with a tent 420b having sloped ends and sides with a horizontal top; the float tent 400c can have an oblong-shaped pool 410c for a subject 402c to float in with a semi-domed tent 420c; or the float tent 400d can have a quadrilateral-shaped pool 410d for a subject 402d to float in with a triangle tent 420d that has at least one vertical tent wall. However, other shapes and configurations can be used.

Figure 5:
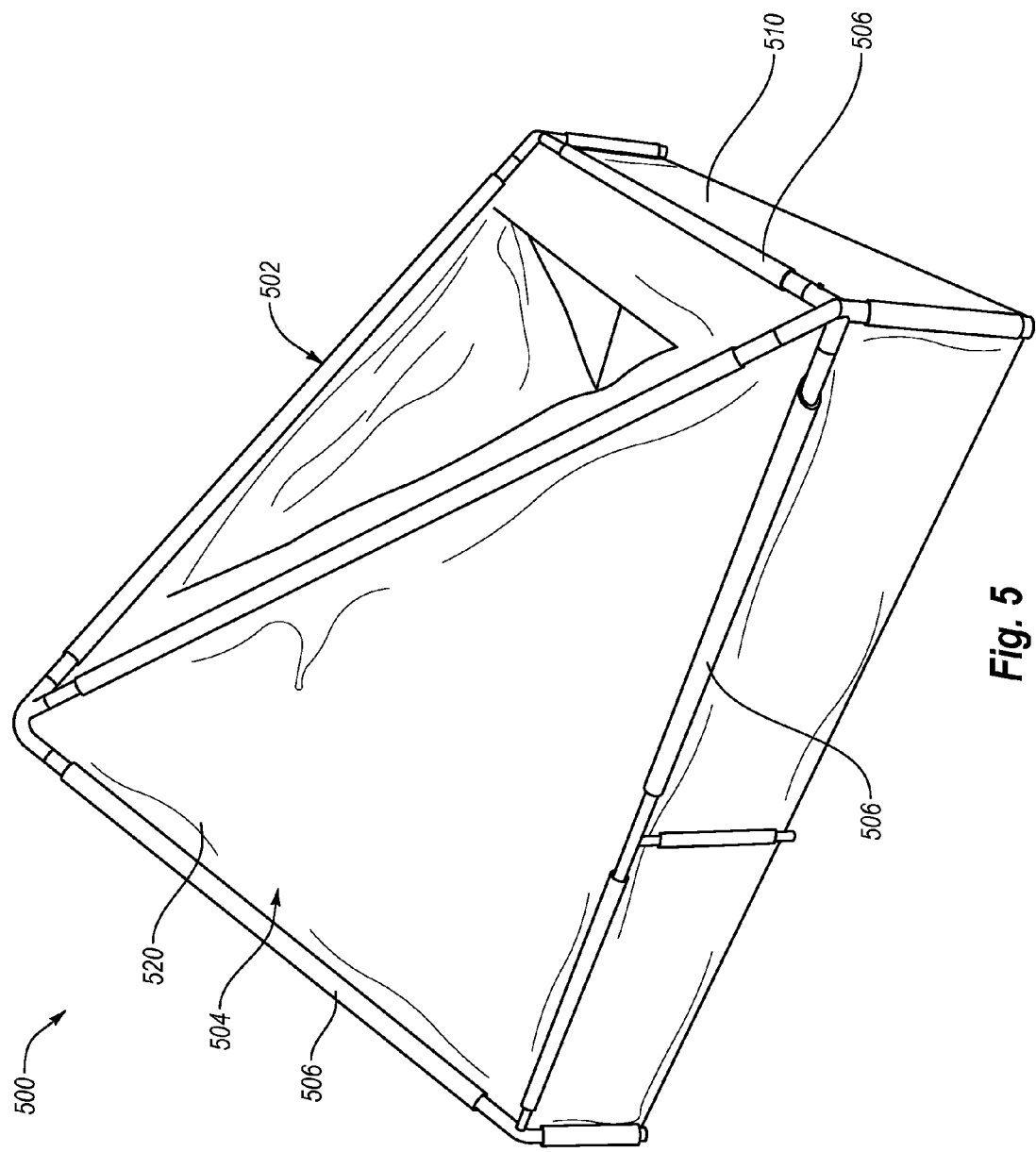
FIG. 5 includes an illustration of an embodiment of a float tent.

FIG. 5 illustrates another embodiment of a float tank 500 that includes two separate elements: the float tent exterior frame 502; and the pool tent 504 having the pool 510 and the tent 520. The pool tent 504 is hung from the exterior frame 502 and coupled therewith. The pool tent 504 can include sleeves 506 that receive the exterior frame 502 so that the pool tent 504 hangs therefrom. However, other coupling can be used, such as straps, ties, or the like. Also, the exterior frame 502 can provide an external support to the pool portion 510 as well as the tent portion 520. The tent portion 520 and pool portion 510 may be separate members. Alternatively, the tent portion 520 and pool portion 510 can be a unitary member, such as by the canvas welded together. The frame can be configured as described herein.

In one embodiment, the tent can be a heavy duty waterproof canvas that fits over a pool base and corresponding frame. The pool can also be heavy duty waterproof canvas that is designed to be filled with water up to 10 inches, for example. The material of the tent and/or pool can be opaque so that substantially or no light penetrates, such as light for an ordinary house lamp or lightbulb. The internal or external surface of the tent and/or pool can be black to inhibit light penetration.

In one embodiment, the tent and/or pool can be prepared with sheets that include insulation sufficient to insulate the walls of the one or more of the walls of the tent, walls of the pool, or base of the pool. The insulated walls and base can be from any type of insulation. The insulation can be provided by two layers of canvas with one or more air pockets therebetween. The insulation can be provided with one or more layers of canvas with an insulating panel associated therewith. The insulation can be can be any type of insulation configuration that allows the float tent to more efficiently retain heat to inhibit temperature decreases and reduce operating costs of the heater.

The material of the float tent can be any waterproof material; however, waterproof canvas can be used. The waterproof canvas can be stitched together in accordance with the designs herein. Alternatively, the waterproof canvas can be welded together and omit stitching, which can improve the waterproof capabilities as well as the sensory deprivation capabilities. In one aspect, the outside surface can be a white, such as all white or salt white color. The white color can mask salt residue to enhance the appearance of the float tent. Similarly, while the interior surface can be black, the black can be an internal layer, and the inside surface may also be white to mask salt residue.

In one aspect, the frame can be stainless steel, and can use quick connect and disconnect couplings to couple the frame members together.

In one embodiment, the tent can be a 4-sided pyramid. However, other shapes can be used.

In one embodiment, the float tent can include a radiant heater, which is shown as radiant heater 157, as shown in FIG. 1B. The radiant heater 147 can be a mat that can be heated by another heater or heated by electricity. For example, the water heater in the float tent can heat the radiant heater 157, which can then retain heat to maintain the temperature. Alternatively, an electric power supply can cause the radiant heater 147 to heat. The radiant heater can be silent, which can enhance the floating and sensory deprivation as well as other therapeutic purposes. The radiant heater can also include thermocouples and controllers for precise temperature control in order to obtain the temperature parameters described herein. The radiant heater can be included in a float tent kit. Such a float tent kit can include any of the components described herein.

In one aspect, the float tent can include vents, which can be pipes passing through the tent (e.g., PVC pipe) that includes an elbow or turn to inhibit light from entering into the tent.

In one aspect, the pump can be configured with a filter, and may include a mechanical filter and a UV filter. This pump may also include ozone or other units for cleansing the water.

In one embodiment, the float tent can include a heater that can self-regulate temperature by including sufficient thermocouples and components and electronics to modulate the temperature and to obtain a desired temperature of the water in the pool. In one aspect, the water can be heated with unique under-tank heaters that heat the water to skin temperature so the user can't feel the difference between the water and air in the float tent. A custom heater with temperature control can hold the water to within +/−1 degree with an integrated thermometer or thermostat system. The heater can operate at or near skin temperature, releasing a subtle, gentle heat into the water when needed. This results in a stable water temperature to encourage a deeper, more peaceful float. Even during longer floats there is no overall heat loss as the heater instantly responds to the smallest temperature change. The heater can be configured to substantially eliminate electromagnetic radiation (EMF) from the float environment to improve floatation experiences.

In one embodiment, the pool base of the float tent can include a base surface having insulation, where the insulation can be coupled or affixed with the base surface or the insulation can be a separate member that is placed into or under the base member of the pool. The insulating member can isolate the water from the ground, and thereby reduce noise while insulating the base. This allows less heating to maintain the proper or desired temperature that is set with the heater. The insulating member can be a radiant heat mat.

In one embodiment, the water in the tent can have 800 pounds of Epsom salt dissolved into the pool (e.g., pool having 4 feet by 8 feet with water depth of 10 inches) so when a person is in the water, they float completely and effortlessly. However, other salts or other salt amounts can be used to facilitate floating. The water can be brine, which can range from about 3.5% or 5% to about 40% salt solution (e.g., salinity). The water may be saturated with the salt at a temperature of about 95° F. to 105° F., from 97° F. to 102° F., or about 98° F. to 99° F. In one example, the water can have salt at from 250 to 500 parts per thousand (PPT), from 300 to 400 PPT, from 325 to 375 PPT, or about 350 PPT at operating temperature which is skin temperature. Skin temperature can usually range from 97° F. to 99.6° F. However, the water can be adjusted to 98.6° F. The salt can be any salt or mixture of salts. The water may be supersaturated by first heating the water to a much higher temperature, saturating the water with salt, and then lowering the water to operating temperature. In any embodiment, the water has sufficient salt to facilitate effortless floatation of a human subject, which can be a child, teen, or adult, and which may range in weights. The amount of salt can drastically vary depending on a number of circumstances. Accordingly, an embodiment of the invention includes the float tent and a sufficient amount of salt to float the user. As such, 800 pounds of Epsom salt can be used as an example +/−10%, 20%, 30%, 40%, 50%, 60%, or more for a pool having 4 feet by 8 feet with water depth of 10 inches. These parameters can be used to calculate the salinity or saturation, which can be applied to other water volumes in accordance with the invention.

In one aspect, the salt can be added to the water to obtain at least about 60% saturation, at least about 70% saturation, at least about 75% saturation, at least about 80% saturation, and at least about 90% saturation. In one embodiment, the saturation can be about 99-100%.

In one aspect, the heater can heat the water to a temperature at least about 90° F., at least about 91° F., at least about 92° F., at least about 93° F., at least about 94° F., at least about 95° F., at least about 96° F., at least about 97° F., or at least about 98° F., or be about 93° F. to 105° F., from 94° F. to 102° F., or about 95° F. to 99° F. In one example, the water is set at about 93.5° F.

In one embodiment, the float tent can include a water pump to circulate the water. The pump can circular the water periodically or sporadically to keep the water clean when not in use. Such water pumps are well known.

In one embodiment, the float tent can include a UV sterilization unit that uses UV light to sterilize or otherwise kill harmful microbes. Such UV units are well known.

In one embodiment, the float tent can include an ozone unit that produces ozone and introduces the ozone in the water to kill harmful microbes. Such ozone units are well known. Optionally, the pump and/or UV unit and/or ozone unit can be combined into a single unit as is common with hot tubs.

In one embodiment, the floatation unit can include a filter unit to filter the water to cleanse contaminants from the water. The filter unit can include a micron bag filter to keep the water clean. The filter unit can be associated with the pump or include in the pump unit so that the pump pumps water through the filter.

In one embodiment, the shape and design of the tent can be configured for enhancing or otherwise improving the user experience during use, such as in relaxation, meditation, or sensory deprivation. The angle of the tent walls can be designed to repel humidity and prevent condensation accumulation and distracting water drips from the ceiling of the tent that may otherwise interrupt a relaxing or peaceful float session. The tent can also be big enough that the user can lie down in a relaxed position without touching or hitting any side wall or ceiling in any direction. This tent walls can be lightproof or opaque so once the user is inside and the entrance is closed, the user can't see anything and almost pitch black or lightlessness can be achieved.

In one embodiment, the frame structure can include supports and coupling members that are configured to inhibit corrosion from salt. The supports can be hard plastics, composites, or metal alloys that are anti-corrosive. For example, the metal alloy can be any stainless steel to inhibit the formation of rust due to possible salt contact.

In one embodiment, the frame can be configured to be collapsible so that the float tent can be set up and taken down easily. For example, the supports and coupling members can snap together or have any coupling that allows for easy setup and takedown. The pool and/or tent can also include loops or other structures that couple the material of the tent and/or pool with the frame members. FIG. 3 shows the support members 306 passing through sleeves of the pool material. Also, FIG. 3 shows the bottom supports are excluded and only the corner supports provide the legs for the support of the frame.

In one embodiment, the angle of the tent walls is designed to inhibit condensation dripping back into the pool. There are a wide range of angles that can inhibit condensation dripping. It should be recognized that different materials with different properties (e.g., hydrophobicity compared to hydrophilicity) or surface treatments (e.g., smooth compared to rough) will have different angles that inhibit condensation drip. The angles can be a minimum of 1 inch vertical distance for every horizontal foot; however, steeper wall angles may be better such as 2 inches vertical distance for every horizontal foot, 4 inches vertical distance for every horizontal foot, 6 inches vertical distance for every horizontal foot, 8 inches vertical distance for every horizontal foot, 10 inches vertical distance for every horizontal foot, 12 inches vertical distance for every horizontal foot, 14 inches vertical distance for every horizontal foot, or steeper. Examples of angles can range from at least about 4.75 degrees, 9.15 degrees, 18.42 degrees, 26.74 degrees, 30 degrees, 40 degrees, 45 degrees, 60 degrees, or any value or range therebetween.

In one embodiment, the float tent can include the following features: 24/7 filtration, including when not in use; extremely low interior condensation; under-body heater, which can maintain constant temperature during floatation; UV sterilization; air venting to bring fresh air into the float tent; multicolor LEDs, which can be configured to pause on select colors (e.g., mood colors) or for strobe effects, or starry sky simulation; music capability (e.g., plugin for music device or Bluetooth); all components removable; silent pump motor, with one or multiple jets for better water flow; and internal or external control system and session control.

In one embodiment, the float tent can include a large opening that offers an easier entrance and ease of use compared to the top hatch type lid common to float tanks. Float tents are rigid and not portable; however, the float tank can be fabric and be flexible for portability when the frame is collapsible or can be disassembled easily. The large opening also gives easier access for the able and the less abled. In one aspect, conveniently positioned internal grab handles offer greater safety, comfort and sense of security for the user. The handles can be positioned near the opening.

In one embodiment, the float tent can include an interior that is selectively lit by one or more underwater LED lights in any color, which can be set or change, such as a rich, vibrant blue. The lighting can be configured or programmed to gently fade in and out, and which may be controlled at the touch of the interior switch to enhance the peace of the floatation environment. Mood and color-changing lighting may also be available in the ceiling, such as distributed across the roof (e.g., star patterns) and highlighting the float tent.

In one embodiment, the float tent can include a supplemental insulating cover that fits over the tent portion and optionally also over the pool portion to touch the ground. The supplemental insulating cover can be as illustrated in FIG. 3.

In one embodiment, a user can use the float tent for relaxation, meditation, sensory deprivation, or other floating use. For example, the use can be floating in about 10 inches of water saturated with over 800 pounds of Epsom salts, which can simulate a near-zero gravity environment. The water is heated to skin temperature, which dulls the sense of touch. After a while, the user may not even feel the water. This allows the user to feel weightless, such as floating through space. The float tent environment can allow for no distractions, just stillness. This allows the stresses and worries to fade away. After a float tent session, the user's physical body can feel light and energized. Also, any physical pain experienced prior to the float tent session may slowly fade as inner peace arises. For example, the float tent can be used for: diminished physical pain, including chronic pain; accelerated healing; spinal decompression; stress relief; mental relaxation; enhanced creativity and learning; pregnancy relief; help with depression and anxiety; strengthened immune system; assistance in a more restful sleep (e.g., for those with insomnia); increased energy; enhanced mental focus and problem solving; anger management; deep meditation; or the like. Also, the float tent can be used to help treat or relieve symptoms of: arthritis, back pain, premenstrual tension, postpartum depression, asthma, migraine headaches, multiple sclerosis, cardiovascular conditions, osteoporosis, synovitis, and fibromyalgia, among others.

During use of the float tent, the float tent environment can leave the user feeling disconnected and isolated from the normal world of perception. This experience can be very relaxing and therapeutic for the mind as it does not have to take in or monitor normal senses. It is a great environment to think with extra brain power. Also, it presents the perfect meditation environment with the lack of mental stimulus.

In one embodiment, the float tent can be configured for use in sensory deprivation floatation therapy. Sensory deprivation therapy utilizes floating as a method of attaining the deepest relaxation a user can experience. This type of sensory deprivation therapy can help to ease a number of medical conditions and symptoms. During such a use, the lights, sounds, or other distractions that may arise from the components can be turned off or excluded.

In one embodiment, a float tent can include: a frame having a pool frame portion with a tent frame portion thereof over the pool frame portion; a tent having the tent frame portion, the tent having a closable opening; and a pool having the pool frame portion, the pool having pool sides dimensioned to hold at least 8 inches of water and having a pool base dimension sufficient for a person to lay in the pool without touching pool sides. In one aspect, the tent can include tent walls having an angle that inhibits condensation drip, the angle being with respect to the pool base. In one aspect, the angle is at least 4.5 degrees. In one aspect, the tent includes a material that is opaque. In one aspect, the float tent includes a heater configured to heat the water to skin temperature of the person. In one aspect, the float tent includes a water circulation pump and filter. In one aspect, the float tent includes all tent walls having the condensation drip inhibiting angle. In one aspect, the tent includes a tent member and the pool includes a pool member that is separate from the tent member. In one embodiment, the frame includes frame supports and frame coupling members that are configured for assembling and disassembling the float tent. In one aspect, each tent wall is a triangle with a base dimensioned with a pool wall of the pool.

In one embodiment, a method of floatation can include: providing the float tent as described herein, the float tent having water in the pool that has at least about 3.5% salinity and at least about 95° F.; and floating a subject in the water of the pool without touching the pool base or pool walls. In one aspect, the method can include inhibiting light and/or sound from entering into the float tent. In one aspect, the method can include the subject floating without their arms or legs touching another part of their body. In one aspect, the method can include the user floating until having one or more of the following: diminished pain; accelerated healing; spinal decompression; stress relief; mental relaxation; enhanced creativity and learning; pregnancy relief; relief from depression and/or anxiety; strengthened immune system; attainment of a more restful sleep; increased energy; enhanced mental focus; improved anger management; deep meditation; or combinations thereof. In one aspect, the method can include the user floating until improving: arthritis, back pain, premenstrual tension, postpartum depression, asthma, migraine headaches, multiple sclerosis, cardiovascular conditions, osteoporosis, synovitis, fibromyalgia, or combinations thereof.

In one embodiment, a float tent kit can include un-assembled components of the float tent as described herein. Such a float tent kit can include: a float tent frame; a pool base configured to retain water, the pool base having pool sides dimensioned to hold at least 8 inches of water and having a pool base dimension sufficient for a person to lay in the pool without touching pool sides; and a tent having a closable opening. The float tent frame, pool base, and tent are configured to be assembled into a float tent. The float tent frame has a pool frame portion with a tent frame portion thereof over the pool frame portion. The tent is configured to be received onto the tent frame portion. The pool base is configured to be received onto the pool frame portion. In one aspect, the float tent kit can include a heating unit. In one aspect, the float tent kit can include a water circulation pump and filter. In one aspect, the float tent kit can include one or more of: a salt reservoir, a UV unit; an ozone unit; a timer; a light device; or a sound device. In one aspect, the float tent kit can include an amount of salt sufficient to create water salinity in the pool base of at least 3.5% salinity.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

The invention claimed is:

1. A therapeutic float tent providing a sensory deprivation state for a user in order to inhibit light, temperature, and physical stimulus to the user while floating in the float tent, comprising:
   a frame including a number of supports and support-connecting joints, the frame having a pool frame portion defining a shape of a pool;
   a tent frame portion disposed over the pool frame portion thereby defining a shape of a tent;

the tent including flexible having as least one opaque light inhibiting tent walls coupled to, and being shaped by, the tent frame portion, the tent including at least one closable opening in one of the tent walls;

an electrical radiant heater configured to heat water in the pool and maintain the temperature of the water between 95 and 99.6 degrees Fahrenheit; and the pool having flexible water-proof pool walls coupled to and being shaped by the pool frame portion, the pool having pool sides formed by the pool walls and dimensioned to hold less than 12 inches deep of water between a base of the pool and a surface of the water and having the pool base defined by the pool walls and dimensioned sufficient for a person to float in the water of the pool without touching the pool sides or the base of the pool.

2. The float tent of claim 1, wherein the tent walls are made of a single sheet of flexible polymer lined material and have an angle greater than 45 degrees that inhibits condensation drip, the angle being with respect to the pool base.

3. The float tent of claim 1, wherein:
the float tent is configured for the tent walls to be external to the tent frame portion and coupled therewith; and
the pool walls are internal to the pool frame portion and coupled therewith.

4. The float tent of claim 1, comprising a water circulation pump and a filter located within the pool.

5. The float tent of claim 1, wherein the pool frame portion includes horizontal pool frame supports coupled to frame coupling members and vertical pool frame supports coupled to the frame coupling members and tent frame supports coupled to the frame coupling members.

6. The float tent of claim 1, wherein the pool is rectangular shaped and each tent wall is triangular shaped with a base dimensioned so that each tent wall meets at an angle with respect to one of the vertical pool walls of the pool, the sides of the pool being less than 28 inches high and the tent walls are angled from the side of the pool to a center of the pool.

7. The float tent of claim 1, the tent including at least one skirt wall that covers the pool sides.

8. The float tent of claim 1, wherein the heater includes a radiant heat mat and insulation disposed at or under a base surface of a pool base of the float tent.

9. The float tent of claim 1, the sides of the tent being integrated with the pool sides.

10. A method of providing a therapeutic floatation experience for a subject, the method comprising:
assembling a float tent, including:
assembling a frame including:
assembling a pool frame portion including a number of poles and joints defining a shape of a pool; and
assembling a tent frame portion including a number of poles and joints defining a shape of a tent disposed over the pool;
assembling the tent supported by the assembled tent frame portion, the tent being made of an opaque material that inhibits light from entering the interior of the pool, the tent walls being coupled to, and being shaped by, the tent frame portion, at least one of the tent walls having a closable opening; and
assembling the pool supported by the assembled pool frame portion, the pool having flexible water-proof pool walls coupled to and being shaped by the pool frame portion, the pool being designed to hold no more than 12 inches deep of water between a base of the pool and a surface of the water when the water is held by the pool, a perimeter of the pool base being defined by the pool walls with dimensions sufficient for a person to lay in 12 inches or less of water above the base of the pool without touching the pool sides;
filling the pool of the float tent with water and adding salt to the water such that the water has at least 3.5% salinity to a depth of no more than 12 inches deep;
heating the water to at least 95° F. using an electrical radiant heater; and
floating a subject in the water of the pool without the subject touching the pool base or pool walls.

11. The method of claim 10, further comprising the subject floating without their arms or legs touching another part of their body.

12. The method of claim 10, further comprising the subject floating for a duration until having one or more of the following therapeutic responses: diminished pain; accelerated healing; spinal decompression; stress relief; mental relaxation; enhanced creativity and learning; pregnancy relief; relief from depression; relief from anxiety; strengthened immune system; attainment of a more restful sleep; increased energy; enhanced mental focus; improved anger management; deep meditation; or combinations thereof.

13. The method of claim 10, further comprising the subject floating for a duration to improve: arthritis, back pain, premenstrual tension, postpartum depression, asthma, migraine headaches, multiple sclerosis, cardiovascular conditions, osteoporosis, synovitis, fibromyalgia, or combinations thereof.

14. The method of claim 10, further comprising:
dis-assembling the float tent, including:
dis-assembling the tent from the assembled tent frame portion;
dis-assembling the pool from the assembled pool frame portion; and
dis-assembling the frame including:
dis-assembling the pool frame portion from defining the shape of the pool; and
dis-assembling the tent frame portion from defining the shape of the tent disposed over the pool.

15. The method of claim 10, further comprising heating the water to more than 97° F. but less than 99.6° F. using the electrical radiant heater, wherein the heater is configured to substantially eliminate electromagnetic radiation (EMF) from the float environment to improve floatation experience.

* * * * *